United States Patent
Zhang et al.

(10) Patent No.: US 11,254,665 B2
(45) Date of Patent: Feb. 22, 2022

(54) CRYSTALLINE SULFAMIDE COMPOUND

(71) Applicants: CHIA TAI TIANQING PHARMACEUTICAL GROUP CO., LTD., Jiangsu (CN); LIANYUNGANG RUNZHONG PHARMACEUTICAL CO., LTD., Jiangsu (CN); CENTAURUS BIOPHARMA CO., LTD., Beijing (CN)

(72) Inventors: Xiquan Zhang, Lianyungang (CN); Wenwei Xu, Lianyungang (CN); Mingming Li, Lianyungang (CN); Minmin Kong, Lianyungang (CN); Shufeng Wu, Lianyungang (CN); Aiming Zhang, Lianyungang (CN)

(73) Assignees: CHIA TAI TIANQING PHARMACEUTICAL GROUP CO., LTD., Lianyungang (CN); LIANYUNGANG RUNZHONG PHARMACEUTICAL CO., LTD., Lianyungang (CN); CENTAURUS BIOPHARMA CO., LTD., Beijing (CN)

( * ) Notice: Subject to any disclaimer, the term of this patent is extended or adjusted under 35 U.S.C. 154(b) by 46 days.

(21) Appl. No.: 16/649,120

(22) PCT Filed: Sep. 21, 2018

(86) PCT No.: PCT/CN2018/106889
§ 371 (c)(1),
(2) Date: Mar. 19, 2020

(87) PCT Pub. No.: WO2019/057142
PCT Pub. Date: Mar. 28, 2019

(65) Prior Publication Data
US 2020/0291012 A1    Sep. 17, 2020

(30) Foreign Application Priority Data

Sep. 22, 2017   (CN) ......................... 201710863924.8

(51) Int. Cl.
*C07D 417/04*    (2006.01)

(52) U.S. Cl.
CPC ........ *C07D 417/04* (2013.01); *C07B 2200/13* (2013.01)

(58) Field of Classification Search
CPC .................................................. C07D 417/04
See application file for complete search history.

(56) References Cited

U.S. PATENT DOCUMENTS

| | | |
|---|---|---|
| 9,850,277 B2 | 12/2017 | Popovici-Muller et al. |
| 2013/0184222 A1 | 7/2013 | Popovici-Muller et al. |
| 2015/0087600 A1 | 3/2015 | Popovici-Muller et al. |
| 2017/0007661 A1 | 1/2017 | Gu |
| 2021/0047314 A1* | 2/2021 | Zhu ...................... A61K 31/433 |

FOREIGN PATENT DOCUMENTS

| | | |
|---|---|---|
| CN | 103097340 A | 5/2013 |
| CN | 104136411 A | 11/2014 |
| JP | 2015511217 A | 4/2015 |
| JP | 2016525130 A | 8/2016 |
| JP | 2017508804 A | 3/2017 |
| WO | 2015/010297 A1 | 1/2015 |

(Continued)

OTHER PUBLICATIONS

Kakkar et al. Drug Development and Industrial Pharmacy p. 1063-1067. (Year: 1997).*
Bleeker, E., F., et al., "IDH1 Mutations at Residue p. R132 (IDH1(R132)) Occur Frequently in High-Grade Gliomas But Not in Other Solid Tumors," Human Mutation, vol. 30, Issue 1, pp. 7-1 (2009).
Green, A., et al., "Somatic Mutations of IDH1 and IDH2 in the Leukemic Transformation of Myeloproliferative Neoplasms," The New England Journal of Medicine, vol. 362:369-370 (Jan. 28, 2010).

(Continued)

*Primary Examiner* — Emily A Bernhardt
(74) *Attorney, Agent, or Firm* — Maschoff Brennan

(57) ABSTRACT

The present application relates to a crystalline sulfamide compound, and in particular relates to a crystalline (S)—N—((S)-1-(2-chlorphenyl)-2-((3,3-difluorocyclobutyl) amido)-2oxoethyl)-2-(4-cyanopyridin-2-base)-N-(3-fluoro-phenyl)-isothiazolidine-3-formamide 1,1-dioxide, and a preparation method therefor, a crystalline composition, a pharmaceutical composition and uses thereof. An X-ray powder diffraction spectrum of a crystalline hydrate of formula II of the present application has diffraction peaks at positions of about 14.40°, 20.28°, 20.94°, 22.02°, and 24.46°, represented by 2θ. The crystalline hydrate of formula II of the present application has good IDH1 inhibitory activity and performs high stability, and therefore has advantages in physical property, safety and metabolic stability, and has high medicine value.

(II)

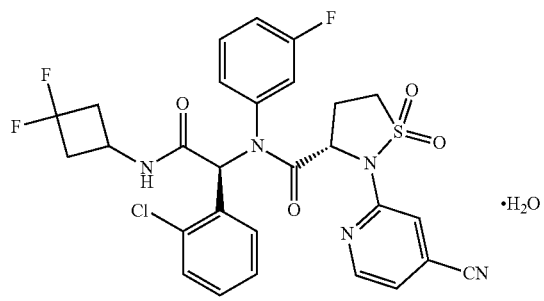

20 Claims, 5 Drawing Sheets

(56) References Cited

FOREIGN PATENT DOCUMENTS

WO 2017/162157 A1 9/2017

OTHER PUBLICATIONS

"Stability Testing of New Drug Substances and Products," in ICH Q1A and "Guidelines for the Stability Testing of Drug Substances and Preparations" in Pharmacopoeia of China, fourth part, 2015 edition, 9001.

\* cited by examiner

CRYSTALLINE SULFAMIDE COMPOUND

CROSS-REFERENCE TO RELATED APPLICATIONS

This application claims the priority and benefits of Chinese Patent Application No. 201710863924.8, filed on Sep. 22, 2017 before the State Intellectual Property Office of the People's Republic of China, all the contents of which are incorporated herein by reference in their entirety.

FIELD OF THE INVENTION

The present application belongs to the field of medical technology, and it relates to a crystalline of a sultam compound, and in particularly relates to a crystalline of (S)—N—((S)-1-(2-chlorophenyl)-2-((3,3-difluorocyclobutyl)amino)-2-oxoethyl)-2-(4-cyanopyridin-2-yl-N-(3-fluorophenyl)-isothiazolidine-3-carboxamide 1,1-dioxide, a preparation method therefor, a crystalline composition, a pharmaceutical composition and use thereof.

BACKGROUND OF THE INVENTION

As the most important key enzyme in intracellular tricarboxylic acid cycle, IDH (full name: isocitrate dehydrogenase) can catalyze oxidative decarboxylation of isocitric acid to produce 2-oxoglutarate (i.e., α-ketoglutaric acid). There are two different subtypes of IDH, one using NAD(+) as an electron acceptor and the other using NADP(+) as the electron acceptor. Five types of IDH have been reported, three of which are NAD(+)-dependent isocitrate dehydrogenases, locating in the mitochondrial matrix; and the other two of which are NADP(+)-dependent isocitrate dehydrogenases, wherein one locates in the mitochondria and the other locates in the cytoplasm.

Researchers have shown that many tumors (such as neuroglioma, sarcoma, acute myelocytic leukemia, etc.) have an IDH mutation at arginine residue in a catalytic center (IDH1/R132H, IDH2/R140Q, and IDH2/R172K). In 2009, Bleeker et al. have detected IDH1 mutations in 672 tumor samples obtained from different sources and 84 cell lines from different tumor cell lineages, and found that these mutations specifically and centrally occurred in gliomas (Bleeker et al., 2009. IDH1 mutations at residue p.R132 (IDH1(R132)) occur frequently in high-grade gliomas but not in other solid tumors. Hum Mutat. 30: 7-11). However, the later literature reports have shown that IDH1 mutations also exist in acute myeloid leukemia, prostate cancer, and paraganglioma and the like (Green et al., 2010, Somatic mutations of IDH1 and IDH2 in the leukemic transformation of myeloproliferative neoplasms. N Engl J Med. 362: 369-370). Bleeker et al. found that in IDH1 mutation cases, R132H accounts for 86.9%, and other types such as R132C, R132G, R132L, R132V, and R132S account for a small proportion (Bleeker et al., 2009).

SUMMARY OF THE INVENTION

A sultam compound has the structure shown in formula I, with the chemical name of (S)—N—((S)-1-(2-chlorophenyl)-2-((3,3-difluorocyclobutyl)amino)-2-oxoethyl)-2-(4-cyanopyridin-2-yl)-N-(3-fluorophenyl)-isothiazolidine-3-carboxamide 1,1-dioxide,

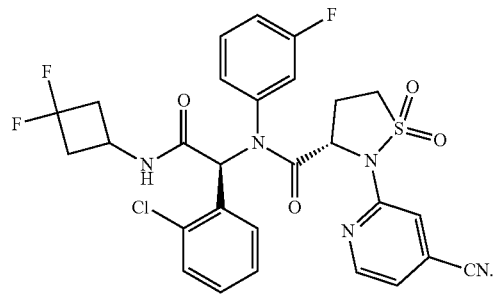

formula I

In one aspect, the present application provides a compound of formula I, characterized in that the compound of formula I is in a crystalline form.

The crystal can be a non-solvate crystal or a solvate crystal, such as a hydrate crystal.

The crystal of the compound of formula I has good IDH1 inhibitory activity, exhibits high stability, and has advantages in physical property, safety, and metabolic stability, with higher medicinal value.

In another aspect, the present application provides a crystalline hydrate of the compound of formula I, wherein the crystal of the hydrate contains 0.5 to 3 water molecules per molecule.

In another aspect, the present application provides a monohydrate represented by formula II,

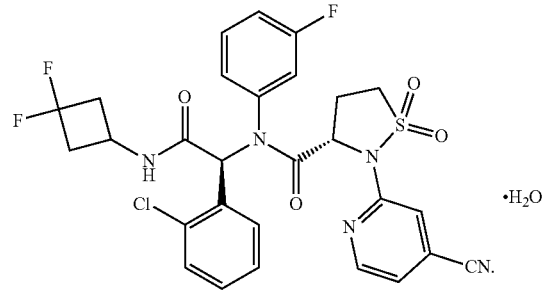

formula II

In an embodiment of the present application, the monohydrate of formula II is in a crystalline form.

In an embodiment of the present application, the crystal of the monohydrate of formula II is characterized in that the X-ray powder diffraction spectrum thereof has diffraction peaks at about 14.40°, 20.28°, 20.94°, 22.02° and 24.46°, represented by 2θ values.

In an embodiment of the present application, the crystal of the monohydrate of formula II is characterized in that the X-ray powder diffraction spectrum thereof has diffraction peaks at about 9.12°, 13.32°, 14.40°, 15.64°, 16.46°, 20.28°, 20.94°, 22.02°, 22.98°, 24.46° and 29.34°, represented by 2θ values.

In an embodiment of the present application, the crystal of the monohydrate of formula II is characterized in that the X-ray powder diffraction spectrum thereof has diffraction peaks at about 5.52°, 9.12°, 13.32°, 14.40°, 15.64°, 16.46°, 19.14°, 19.32°, 20.28°, 20.94°, 21.20°, 22.02°, 22.98°, 23.52°, 24.46°, 26.06°, 29.34° and 31.74°, represented by 2θ values.

In an embodiment of the present application, the crystal of the monohydrate of formula II is characterized in that the X-ray powder diffraction spectrum thereof has diffraction peaks at about 5.52°, 9.12°, 13.32°, 14.40°, 14.90°, 15.64°, 16.46°, 19.14°, 19.32°, 20.28°, 20.94°, 21.20°, 22.02°, 22.98°, 23.52°, 24.46°, 25.74°, 26.06°, 27.32°, 27.98°, 28.90°, 29.34°, 31.00°, 31.74°, 32.22° and 33.32°, represented by 2θ values.

In an embodiment of the present application, the crystal of the monohydrate of formula II is characterized in that the X-ray powder diffraction spectrum thereof has diffraction peaks at about 5.52°, 9.12°, 10.30°, 10.48°, 11.96°, 13.32°, 14.40°, 14.90°, 15.64°, 16.46°, 17.28°, 17.58°, 18.60°, 19.14°, 19.32°, 20.28°, 20.94°, 21.20°, 22.02°, 22.98°, 23.52°, 24.46°, 25.74°, 26.06°, 26.74°, 27.32°, 27.98°, 28.40°, 28.90°, 29.34°, 30.36°, 31.00°, 31.74°, 32.22°, 32.82°, 33.32° and 37.84°, represented by 2θ values.

In an embodiment of the present application, the peak positions and intensity of the characteristic peaks in the X-ray powder diffraction spectrum for the crystal of the monohydrate of formula II have the characteristics as shown in Table 1:

TABLE 1

| Nos. | 2θ (degree) | relative intensity (I/I$_0$) |
| --- | --- | --- |
| 1 | 5.52 | 7 |
| 2 | 9.12 | 25 |
| 3 | 10.30 | 11 |
| 4 | 10.48 | 12 |
| 5 | 11.96 | 8 |
| 6 | 13.32 | 40 |
| 7 | 14.40 | 97 |
| 8 | 14.90 | 15 |
| 9 | 15.64 | 26 |
| 10 | 16.46 | 26 |
| 11 | 17.28 | 10 |
| 12 | 17.58 | 13 |
| 13 | 18.60 | 13 |
| 14 | 19.14 | 28 |
| 15 | 19.32 | 25 |
| 16 | 20.28 | 55 |
| 17 | 20.94 | 100 |
| 18 | 21.20 | 34 |
| 19 | 22.02 | 91 |
| 20 | 22.98 | 35 |
| 21 | 23.52 | 23 |
| 22 | 24.46 | 57 |
| 23 | 25.74 | 17 |
| 24 | 26.06 | 24 |
| 25 | 26.74 | 10 |
| 26 | 27.32 | 19 |
| 27 | 27.98 | 17 |
| 28 | 28.40 | 10 |
| 29 | 28.90 | 15 |
| 30 | 29.34 | 24 |
| 31 | 30.36 | 14 |
| 32 | 31.00 | 20 |
| 33 | 31.74 | 27 |
| 34 | 32.22 | 18 |
| 35 | 32.82 | 12 |
| 36 | 33.32 | 15 |
| 37 | 37.84 | 13 |

In an embodiment of the present application, the X-ray powder diffraction spectrum of the crystal of the monohydrate of formula II is as shown in FIG. 1.

In an embodiment of the present application, the differential scanning calorimetry (DSC) measurement pattern of the crystal of the monohydrate of formula II has an onset point at about 186° C., and an absorption peak at about 193° C.

In an embodiment of the present application, the differential scanning calorimetry (DSC) measurement pattern of the crystal of the monohydrate of formula II is as shown in FIG. 2.

In an embodiment of the present application, the thermogravimetric analysis (TGA) pattern of the crystal of the monohydrate of formula II is as shown in FIG. 3.

In another aspect, the present application provides a crystal composition, wherein the above crystal of the monohydrate of formula II represents 50% or more, preferably 70% or more, still preferably 75% or more, more preferably 80% or more, further more preferably 90% or more, still more preferably 95% or more, and most preferably 98% or more of the weight of the crystal composition. The crystal composition can also comprise a small amount of other crystalline forms or non-crystalline forms of the compound of formula I.

The present application provides a pharmaceutical composition comprising a therapeutically effective amount of the above crystal of the monohydrate of formula II, or the above crystal composition of the monohydrate of formula II. The pharmaceutical composition can comprise at least one pharmaceutically acceptable carrier or other excipients.

In another aspect, the present application provides use of the above crystal of the monohydrate of formula II, the above crystal composition of the crystal of the monohydrate of formula II, or the above pharmaceutical composition in the manufacture of a medicament for treating IDH1 mutation-induced cancer. The above crystal of the monohydrate of formula II, the above crystal composition of the crystal of the monohydrate of formula II, or the above pharmaceutical composition according to the present application can be used alone or in combination with other drugs, for manufacturing a medicament for treating IDH1 mutation-induced cancer.

In another aspect, the present application provides a method for treating IDH1 mutation-induced cancer, which comprises administering a therapeutically effective amount of the above crystal of the monohydrate of formula II, the above crystal composition of the crystal of the monohydrate of formula II, or the above pharmaceutical composition to a mammal in need thereof. The mammal is preferably human.

In another aspect, the present application provides the above crystal of the monohydrate of formula II, the above crystal composition of the crystal of the monohydrate of formula II, or the above pharmaceutical composition for use in treating IDH1 mutation-induced cancer.

In another aspect, the present application provides a non-solvent crystalline form of the compound of formula I.

In an embodiment of the present application, the crystal of the compound of formula I is characterized in that the X-ray powder diffraction spectrum thereof has diffraction peaks at about 8.64°, 9.34°, 20.72°, 21.30°, and 24.02°, represented by 2θ values.

In an embodiment of the present application, the crystal of the compound of formula I is characterized in that the X-ray powder diffraction spectrum thereof has diffraction peaks at about 8.64°, 9.34°, 14.62°, 19.66°, 20.04°, 20.46°, 20.72°, 21.30°, 22.46°, 24.02°, and 27.42°, represented by 2θ values.

In an embodiment of the present application, the crystal of the compound of formula I is characterized in that the X-ray powder diffraction spectrum thereof has diffraction peaks at about 8.64°, 9.34°, 14.62°, 15.18°, 16.36°, 17.04°, 17.60°, 18.40°, 19.66°, 20.04°, 20.46°, 20.72°, 21.30°, 22.16°, 22.46°, 24.02°, 27.42°, 28.46° and 30.16°, represented by 2θ values.

In an embodiment of the present application, the crystal of the compound of formula I is characterized in that the X-ray powder diffraction spectrum thereof has diffraction peaks at about 8.64°, 9.34°, 14.62°, 15.18°, 16.36°, 17.04°, 17.60°, 18.14°, 18.40°, 18.88°, 19.66°, 20.04°, 20.46°, 20.72°, 21.30°, 22.16°, 22.46°, 22.92°, 23.16°, 24.02°, 25.14°, 25.48°, 25.92°, 27.42°, 28.46° and 30.16°, represented by 2θ values.

In an embodiment of the present application, the crystal of the compound of formula I is characterized in that the X-ray powder diffraction spectrum thereof has diffraction peaks at about 8.64°, 9.34°, 11.18°, 12.80°, 13.68°, 14.62°, 15.18°, 15.58°, 16.36°, 17.04°, 17.60°, 18.14°, 18.40°, 18.88°, 19.66°, 20.04°, 20.46°, 20.72°, 21.30°, 22.16°, 22.46°, 22.92°, 23.16°, 24.02°, 24.32°, 24.92°, 25.14°, 25.48°, 25.92°, 26.30°, 27.42°, 27.84°, 28.46°, 30.16°, 30.98°, and 33.18°, represented by 2θ values.

In an embodiment of the present application, the peak positions and intensity of the characteristic peaks of the X-ray powder diffraction spectrum for the crystal of the compound of formula I have the characteristics shown in Table 2:

TABLE 2

| Nos. | 2θ (degree) | relative intensity (I/I$_0$) |
| --- | --- | --- |
| 1 | 8.64 | 25 |
| 2 | 9.34 | 28 |
| 3 | 11.18 | 14 |
| 4 | 12.80 | 14 |
| 5 | 13.68 | 17 |
| 6 | 14.62 | 30 |
| 7 | 15.18 | 23 |
| 8 | 15.58 | 18 |
| 9 | 16.36 | 27 |
| 10 | 17.04 | 25 |
| 11 | 17.60 | 25 |
| 12 | 18.14 | 23 |
| 13 | 18.40 | 28 |
| 14 | 18.88 | 24 |
| 15 | 19.66 | 38 |
| 16 | 20.04 | 33 |
| 17 | 20.46 | 34 |
| 18 | 20.72 | 51 |
| 19 | 21.30 | 100 |
| 20 | 22.16 | 31 |
| 21 | 22.46 | 41 |
| 22 | 22.92 | 23 |
| 23 | 23.16 | 21 |
| 24 | 24.02 | 55 |
| 25 | 24.32 | 19 |
| 26 | 24.92 | 19 |
| 27 | 25.14 | 20 |
| 28 | 25.48 | 24 |
| 29 | 25.92 | 24 |
| 30 | 26.30 | 18 |
| 31 | 27.42 | 30 |
| 32 | 27.84 | 19 |
| 33 | 28.46 | 21 |
| 34 | 30.16 | 24 |
| 35 | 30.98 | 18 |
| 36 | 33.18 | 18 |

In an embodiment of the present application, the X-ray powder diffraction spectrum of the crystal of the compound of formula I is as shown in FIG. 4.

In an embodiment of the present application, the differential scanning calorimetry (DSC) measurement pattern of the crystal of the compound of formula I has an onset point at about 103° C. and an absorption peak at about 130° C.

In an embodiment of the present application, the differential scanning calorimetry (DSC) measurement pattern of the crystal of the compound of formula I is as shown in FIG. 5.

In an embodiment of the present application, the thermogravimetric analysis (TGA) chart of the crystal of the compound of formula I is as shown in FIG. 6.

In an embodiment of the present application, the crystal of the compound of formula I described above can be transformed into the crystal of the monohydrate of formula II in the presence of water, wherein the source of water can be a small amount of water contained in the solvent during preparation, or water in the environment contacted during filtration and drying steps of the preparation, or water in the environment contacted during storage.

In an embodiment of the present application, the crystal of the compound of formula I described above is isolated from all sources of water during the preparation and storage process, thus the obtained crystal of the compound of formula I described above can be in a substantially pure form with respect to the above crystal of the monohydrate of formula II.

In another aspect, the present application provides a crystal composition, wherein the crystal of the compound of formula I described above represents 50% or more, preferably 70% or more, further preferably 75% or more, more preferably 80% or more, further more preferably 90% or more, still more preferably 95% or more, and most preferably 98% or more of the weight of the crystal composition. The crystal composition can also comprise a small amount of other crystalline forms or non-crystalline forms of the compound of formula I, such as the crystal of the monohydrate of formula II.

The present application provides a pharmaceutical composition comprising a therapeutically effective amount of the above crystal of the compound of formula I, or the above crystal composition of the crystal of the compound of formula I. The pharmaceutical composition can comprise at least one pharmaceutically acceptable carrier or other excipients.

In another aspect, the present application provides use of the above crystal of the compound of formula I, the above crystal composition of the crystal of the compound of formula I, or the above pharmaceutical composition in the manufacture of a medicament for treating IDH1 mutation-induced cancer. The above crystal of the compound of formula I, the above crystal composition of the crystal of the compound of formula I, or the above pharmaceutical composition according to the present application can be used alone or in combination with other drugs, for manufacturing a medicament for treating IDH1 mutation-induced cancer.

In another aspect, the present application provides a method for treating IDH1 mutation-induced cancer, which comprises administering a therapeutically effective amount of the above crystal of the compound of formula I, the above crystal composition of the crystal of the compound of formula I, or the above pharmaceutical composition to a mammal in need thereof. The mammal is preferably human.

In another aspect, the present application provides the above crystal of the compound of formula I, the above crystal composition of the crystal of the compound of formula I, or the above pharmaceutical composition for use in treating IDH1 mutation-induced cancer.

In another aspect, the present application provides an amorphous form of the compound of formula I.

In an embodiment of the present application, the X-ray powder diffraction spectrum of the amorphous form of the compound of formula I is as shown in FIG. 7.

In an embodiment of the present application, the differential scanning calorimetry (DSC) measurement pattern of the amorphous form of the compound of formula I has an onset point at about 103° C. and an absorption peak at about 121° C.

In an embodiment of the present application, the differential scanning calorimetry (DSC) measurement pattern of the amorphous form of the compound of formula I is as shown in FIG. 8.

In another aspect, the present application provides a pharmaceutical composition comprising a therapeutically effective amount of the amorphous form of the compound of formula I. The pharmaceutical composition can comprise at least one pharmaceutically acceptable carrier or other excipients.

In another aspect, the present application provides use of the amorphous form of the compound of formula I or the pharmaceutical composition thereof in the manufacture of a medicament for treating IDH1 mutation-induced cancer.

In the present application, the pharmaceutically acceptable carrier may be solid or liquid. The solid carrier can include one or more substance of a flavoring agent, a lubricant, a solubilizer, a suspending agent, filler, a binder, a tablet disintegrant, or an encapsulating material. Suitable solid carriers comprise, for example: magnesium stearate, talc, sucrose, lactose, dextrin, starch, gelatin, cellulose, methyl cellulose, sodium carboxymethyl cellulose, polyvinylpyrrolidone. A liquid carrier is used to prepare compositions such as solutions, suspensions, emulsions, and syrups. Suitable liquid carriers for oral and parenteral administration include water, alcohols, oils and the like.

In the present application, the pharmaceutical composition can be made into a certain dosage form, and the administration route is preferably oral, parenteral (including subcutaneous, intramuscular and intravenous), rectal administration, and the like. For example, the dosage forms suitable for oral administration include tablets, capsules, granules, powders, pills, pulvis, troches, syrups or suspensions; the dosage forms suitable for parenteral administration include aqueous or non-aqueous solutions or emulsions for injection; and the dosage forms suitable for rectal administration include suppositories using hydrophilic or hydrophobic carriers. The above dosage forms can also be made into the dosage forms suitable for rapid release, delayed release or controlled release of the active ingredient as requirement.

The IDH1 mutation described herein has R132X mutation; in some embodiments of the present application, the R132X mutation is selected from R132H, R132C, R132L, R132V, R132S, and R132G; in some preferred embodiments, the R132X mutation is selected from R132H and R132C.

In some embodiments of the present application, the IDH1 mutation-induced cancer is selected from glioblastoma (neuroglioma), myelodysplastic syndrome (MDS), myeloproliferative neoplasm (MPN), acute myeloid leukemia (AML), sarcoma (preferably chondrosarcoma, fibrosarcoma), melanoma, non-small cell lung cancer, bile duct cancer or angioimmunoblastic non-Hodgkin's lymphoma (NHL). In more specific embodiments, the cancer to be treated is neuroglioma, myelodysplastic syndrome (MDS), myeloproliferative neoplasm (MPN), acute myeloid leukemia (AML), bile duct cancer, chondrosarcoma or angioimmunoblastic non-Hodgkin's lymphoma (NHL), etc., preferably including acute myeloid leukemia (AML), myelodysplastic syndrome (MDS), neuroglioma, bile duct cancer or chondrosarcoma.

In another aspect, the present application provides a method for preparing a crystal of the monohydrate of formula II, comprising: (1) dissolving the compound of formula I in an organic solvent, and stirring till the solution is clear; (2) adding water to the solution obtained in step (1); and (3) cooling down the solution to crystallize, filtering and drying.

In some embodiments of the present application, in the preparation method of the crystal of the monohydrate of formula II, the organic solvent in step (1) is selected from one or more (mixed solvents) of methanol, ethanol, isopropanol, ethylene glycol, propylene glycol, acetone, tetrahydrofuran, acetonitrile, dichloromethane, or ethyl acetate; preferably methanol, ethanol or acetone; more preferably methanol or ethanol.

In some embodiments of the present application, in the preparation method of the crystal of the monohydrate of formula II, the molar volume ratio of the compound of formula I to the organic solvent in step (1) is 1 mmol:2-20 mL; preferably 1 mmol:2-15 mL; more preferably, 1 mmol:2-10 mL.

In some embodiments of the present application, in the preparation method of the crystal of the monohydrate of formula II, the temperature for dissolving the compound of formula I in the organic solvent in step (1) is 20° C. to 100° C.; preferably 20° C. to 80° C.; further preferably 20° C. to 60° C.

In some embodiments of the present application, in the preparation method of the crystal of the monohydrate of formula II, the molar volume ratio of the compound of formula I in step (1) to the water in step (2) is 1 mmol:0.01-5 mL; preferably 1 mmol:0.01-3 mL; more preferably 1 mmol:0.05-2 m L.

In some embodiments of the present application, in the preparation method of the crystal of the monohydrate of formula II, the crystallization temperature in step (3) is −10° C. to 25° C.; preferably 0° C. to 10° C.; more preferably 0° C. to 5° C.

In some embodiments of the present application, in the preparation method of the crystal of the monohydrate of formula II, the drying condition in step (3) includes drying at room temperature, drying under reduced pressure or blast drying, and preferably drying under reduced pressure. The drying equipment is a fume hood, a vacuum oven or a blast drying oven, preferably a vacuum oven. The drying temperature is 20° C. to 60° C.; preferably 20° C. to 40° C.; more preferably 30° C. to 40° C.

In some embodiments of the present application, in the preparation method of the crystal of the monohydrate of formula II, in addition to the water added in step (2), the source of water can also be water contained in the organic solvent, or water in the environment contacted due to the opened container during the preparation process, or water in the environment contacted during crystallization, filtration and drying.

In another aspect, the present application provides a method for preparing the crystal of the compound of formula I, comprising: (1) dissolving the compound of formula I in an anhydrous organic solvent, and stirring till the solution is clear, and adding with 4A molecular sieve to dry; (2) filtering the solution under nitrogen protection, and cooling down the filtrate to crystallize; and (3) filtering under nitrogen protection and drying.

In some embodiments of the present application, in the preparation method of the crystal of the compound of formula I, the anhydrous organic solvent in step (1) is selected from one or more (mixed solvents) of dichloromethane, isopropanol, n-hexane, ethyl acetate, or methyl tert-butyl ether; preferably dichloromethane or isopropanol; more preferably dichloromethane.

In some embodiments of the present application, in the preparation method of the crystal of the compound of formula I, the molar volume ratio of the compound of formula I to the anhydrous organic solvent in step (1) is 1 mmol:2-10 mL; preferably 1 mmol:2-8 mL; more preferably 1 mmol:3-5 mL.

In some embodiments of the present application, in the preparation method of the crystal of the compound of formula I, the time for drying by addition of 4A molecular sieve in step (1) is 1 to 4 hours; preferably 1 to 3 hours; more preferably 1 to 2 hours.

In some embodiments of the present application, in the preparation method of the crystal of the compound of formula I, the mass to volume ratio of the 4A molecular sieve to the anhydrous organic solvent in step (1) is 1 g:2-10 mL; preferably 1 g:2-6 mL; more preferably, 1 g:4-6 mL.

In some embodiments of the present application, in the preparation method of the crystal of the compound of formula I, the temperature for dissolving the compound of formula I in the anhydrous organic solvent in step (1) is 20° C. to 100° C.; preferably 20° C. to 80° C.; more preferably 20° C. to 60° C.

In some embodiments of the present application, in the preparation method of the crystal of the compound of formula I, the temperature for crystallization in step (2) is −20° C. to 25° C.; preferably −10° C. to 10° C.; more preferably −10° C. to 0° C.

In some embodiments of the present application, in the preparation method of the crystal of the compound of formula I, the drying condition in step (3) includes drying at room temperature, drying under reduced pressure, or blast drying, and preferably drying under reduced pressure. The drying equipment is a fume hood, a vacuum oven or a blast drying oven, preferably a vacuum oven. The drying temperature is 20° C. to 60° C.; preferably 20° C. to 40° C.; more preferably 30° C. to 40° C.

In another aspect, the present application provides a method for preparing an amorphous form of the compound of formula I, comprising: (1) dissolving the compound of formula I in an anhydrous organic solvent, and stirring till the solution is clear; and (2) concentrating under reduced pressure to give a solid, and drying.

In some embodiments of the present application, in the preparation method of the amorphous form of the compound of formula I, the anhydrous organic solvent in step (1) is selected from one or more (mixed solvents) of ethyl acetate, dichloromethane, methanol, ethanol, and acetone; preferably one or more (mixed solvents) of ethyl acetate, dichloromethane, or methanol; more preferably dichloromethane, or a mixed solvent of ethyl acetate and dichloromethane.

In some embodiments of the present application, in the preparation method of the amorphous form of the compound of formula I, the molar volume ratio of the compound of formula I to the anhydrous organic solvent in step (1) is 1 mmol:1-10 mL; preferably 1 mmol:2-8 mL; more preferably 1 mmol:3-6 mL.

In some embodiments of the present application, in the preparation method of the amorphous form of the compound of formula I, the temperature for dissolving the compound of formula I in the anhydrous organic solvent in step (1) is 20° C. to 60° C.; preferably 20° C. to 40° C.; more preferably 20° C. to 30° C.

In some embodiments of the present application, in the preparation method of the amorphous form of the compound of formula I, the drying condition in step (2) includes drying at room temperature, drying under reduced pressure or blast drying, and preferably drying under reduced pressure. The drying equipment is a fume hood, a vacuum oven or a blast drying oven, preferably a vacuum oven. The drying temperature is 20° C. to 60° C.; preferably 20° C. to 40° C.; more preferably 30° C. to 40° C.

In the present application, the X-ray powder diffraction spectrum for the sample is measured under the following conditions: instrument: Minflex II; pretreatment for sample: direct compression; sample tray: glass tank; DivSlit: 1.25°; SctSlit: 1.25°; RecSlit: 0.3 mm; 2θ angle range: 3-60°; scanning speed 10°/min; Cu target tube pressure and current: 30 KV, 15 mA.

In the present application, the DSC spectrum is measured under the following conditions: instrument: METTLER TOLEDO DSC1; temperature range: 40° C. to 300° C.; heating rate: 10° C./min.

In the present application, TGA thermogravimetric analysis is performed under the following conditions: instrument: NETZSCH TG 209F3; temperature range: 30° C. to 300° C.; heating rate: 10° C./min.

It should be indicated that in the X-ray diffraction spectrum, a diffraction pattern obtained from a crystalline compound is usually characteristic for a specific crystalline form, in which relative intensities of the bands (especially at the low angles) may vary depending upon preferential orientation effects resulting from the differences of crystallization conditions, particle sizes and other measurement conditions. Therefore, the relative intensities of diffraction peaks are not characteristic for a specific crystalline form. It is the relative positions of peaks rather than the relative intensities thereof that should be paid more attention when judging whether a crystalline form is the same as a known crystalline form. In addition, for any given crystalline form, there may be a slight error in the position of the peaks, which is also well known in the field of crystallography. For example, the position of a peak may shift due to the change of a temperature, the movement of a sample, or the calibration of an instrument and so on during analysis of the sample, and the measurement error of the 2θ value is sometimes about ±0.2°. Accordingly, when identifying a crystal structure, such error should be taken into consideration. Usually, the position of a peak is expressed in terms of 2θ angle or lattice spacing d in an XRD pattern and the simple conversion relationship therebetween is d=λ/2 sin θ, wherein d represents the lattice spacing, λ represents the wavelength of incident X-ray, and θ represents the diffraction angle. For the same crystalline form of the same compound, the position of peaks in an XRD spectrum thereof has similarity on the whole, and the error of relative intensities may be larger. In addition, it is necessary to point out that due to some factors such as reduced contents, parts of diffraction lines may be absent in the identification of a mixture. At this time, even a band may be characteristic for the given crystalline form without depending upon all the bands of a high purity sample.

DSC is used to measure a thermal transition temperature for a crystal when absorbing or releasing heat due to the change of its crystalline structure or the melting of the crystal. In a continuous analysis of the same crystalline form of the same compound, the error of a thermal transition temperature and a melting point is typically within a range of about 5° C., typically within about 3° C. When it is said that a compound has a given DSC peak or melting point, it means the DSC peak or melting point ±5° C. DSC provides an auxiliary method to distinguish different crystalline forms. Different crystalline forms can be identified by their characteristically different transition temperatures. It should be pointed out that for a mixture, the DSC peak or melting point may vary within a larger range. In addition, since the melting of a substance is accompanied with decomposition, the melting temperature is related to the heating rate.

Definition

When used in this specification and the appended claims, the following terms have the indicated meanings, unless indicated to the contrary:

"Mammal" includes human; domestic animals, such as laboratory mammals; domestic pets (such as cat, dog, pig, caprine, cattle, sheep, goat, horse, rabbit); and non-domesticated animals, such as wild mammals.

The term "pharmaceutical composition" refers to a formulation of a compound of the present application and a medium generally accepted in the art for delivering a bioactive compound to a mammal, such as human. The medium includes all pharmaceutically acceptable carriers for its use. A pharmaceutical composition facilitates administration of a compound to an organism.

The term "therapeutically effective amount" refers to an amount of a medicament or agent that is non-toxic but can achieve the desired effect. The determination of the effective amount varies with each individual, depending on the age and general condition of the subject, as well as the specific active substance. The appropriate effective amount in each case can be determined by the skilled in the art according to a routine experiment.

In the present application, the "pharmaceutically acceptable carrier" refers to a carrier that does not cause significant irritation to an organism ingesting this carrier, and does not deteriorate the biological activity and properties of an active compound, when administered with the active compound. Other information about carriers can refer to Remington: The Science and Practice of Pharmacy, 21st Ed., Lippincott, Williams & Wilkins (2005), the contents of which are incorporated herein by reference.

In the present application, the "molar ratio" and the "amount-of-substance ratio" are equal to each other.

In the present application, "room temperature" refers to 20° C. to 25° C.

In the present application, the source of anhydrous organic solvents can be commercially available, or obtained by laboratory anhydrous treatment of the commercially available organic solvents. For example, the laboratory treatment method for anhydrous dichloromethane is as follow: dichloromethane is added with calcium hydride, refluxed for 3-4 hours, distilled, and then stored with the 4A molecular sieve.

DETAILED DESCRIPTION

Figure 1:
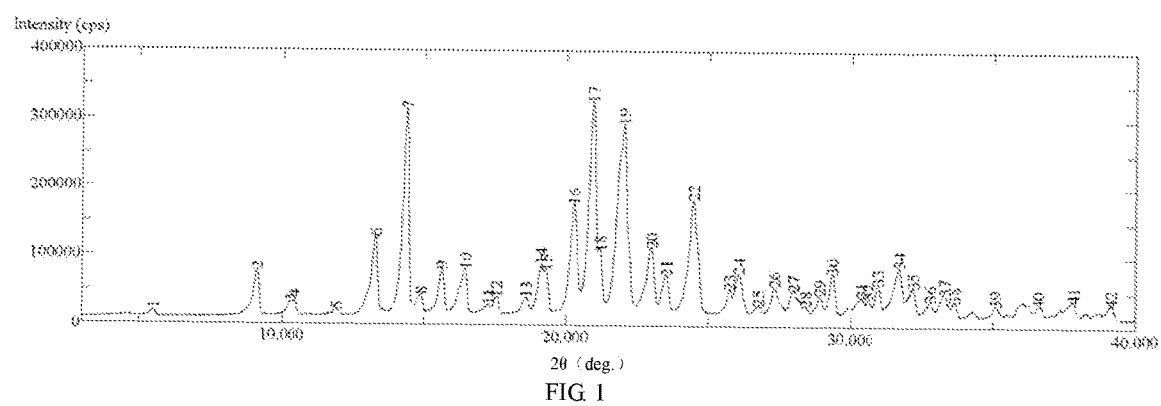
FIG. 1 is an X-ray powder diffraction pattern (XRPD) for the crystal of the monohydrate of formula II in Example 5.
Figure 2:
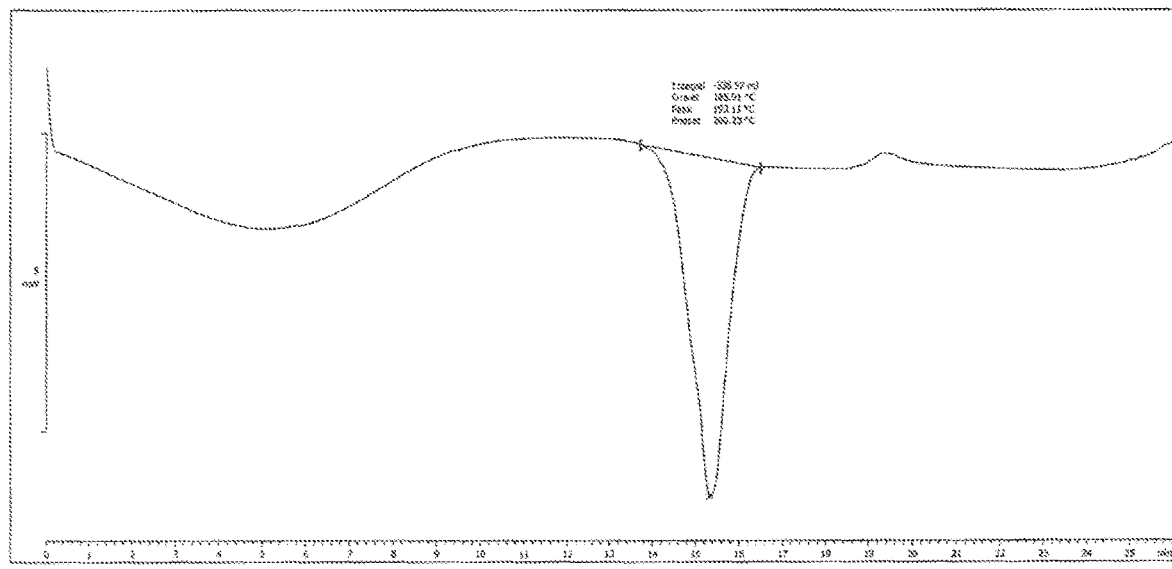
FIG. 2 is a differential scanning calorimetry (DSC) curve for the crystal of the monohydrate of formula II in Example 5.
Figure 3:
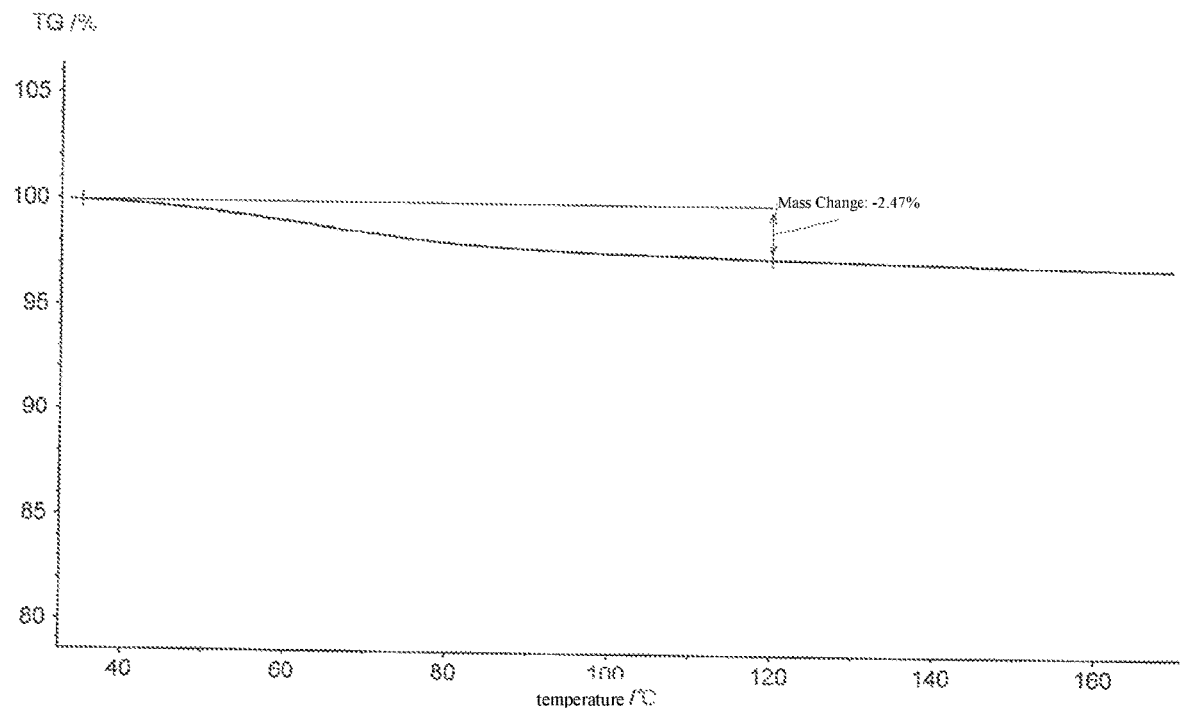
FIG. 3 is a thermogravimetric analysis (TGA) pattern for the crystal of the monohydrate of formula II in Example 5.
Figure 4:
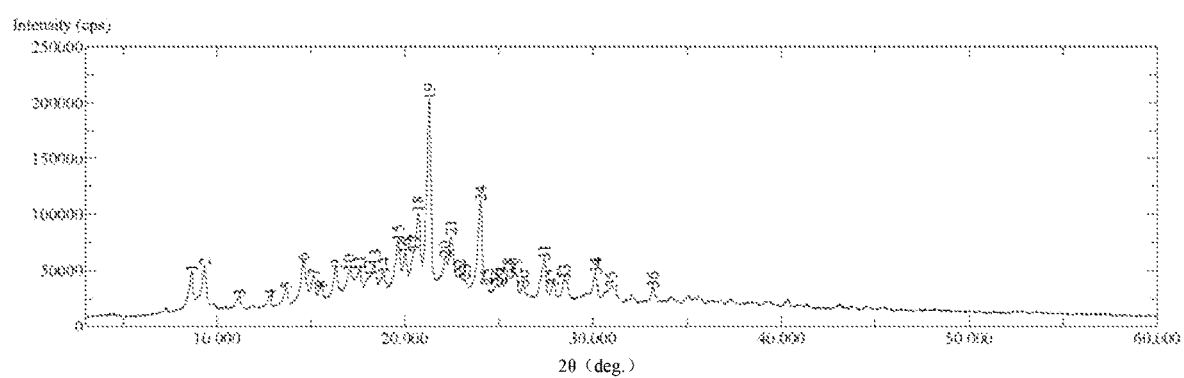
FIG. 4 is an X-ray powder diffraction pattern (XRPD) for the crystal of the compound of formula I in Example 7.
Figure 5:
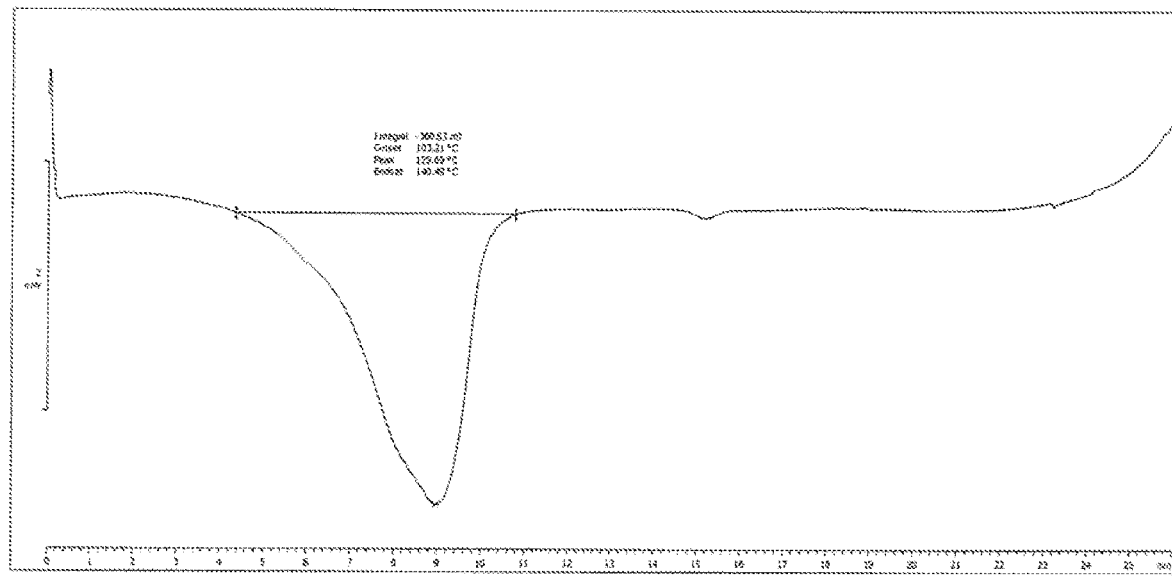
FIG. 5 is a differential scanning calorimetry (DSC) curve for the crystal of the compound of formula I in Example 7.
Figure 6:
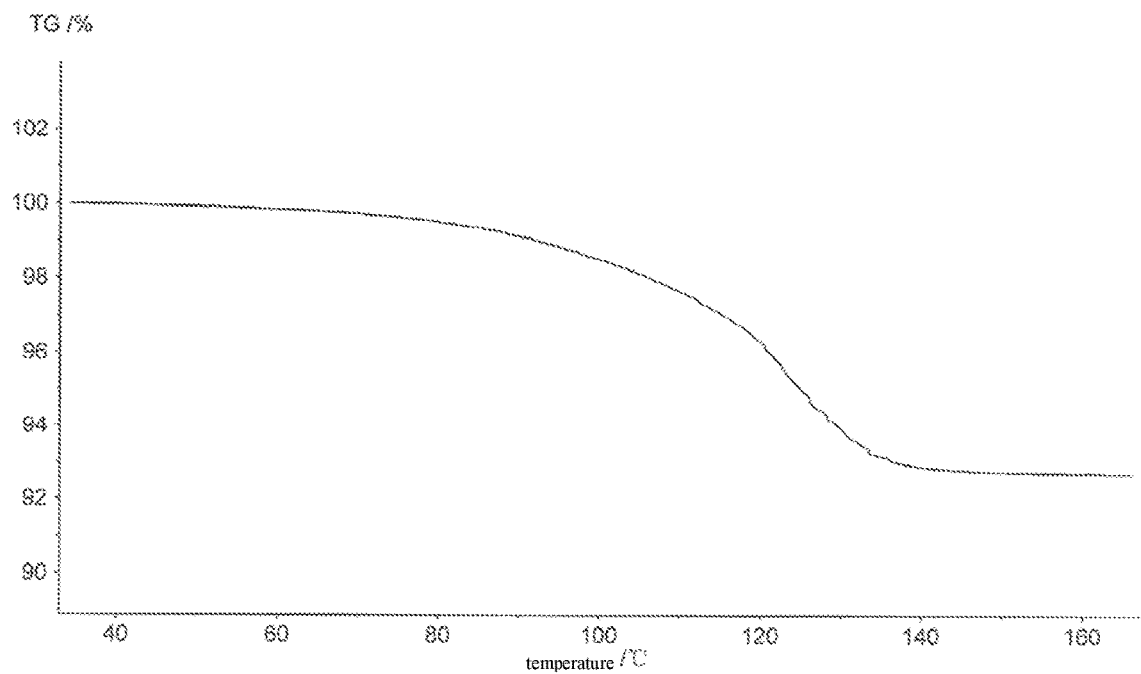
FIG. 6 is a thermogravimetric analysis (TGA) pattern for the crystal of the compound of formula I in Example 7.
Figure 7:
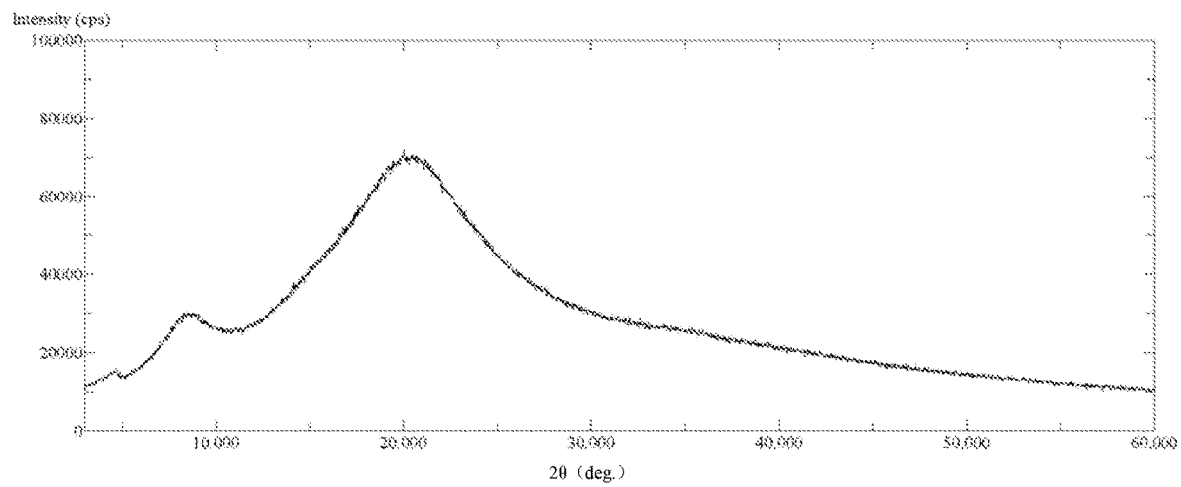
FIG. 7 is an X-ray powder diffraction pattern (XRPD) for the amorphous form in Example 9.
Figure 8:
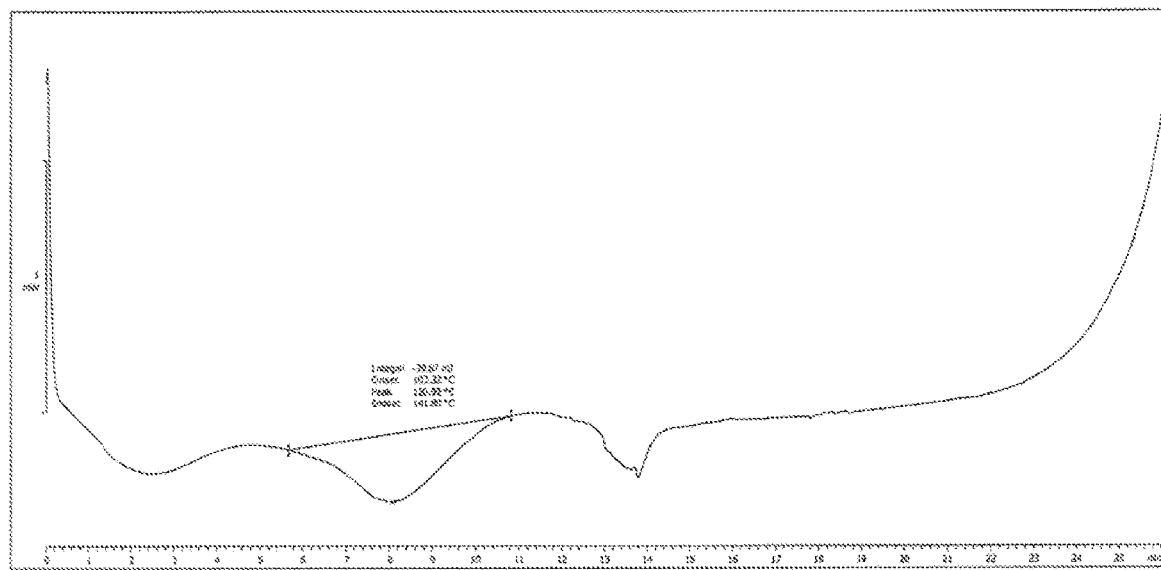
FIG. 8 is a differential scanning calorimetry (DSC) curve for the amorphous form in Example 9.
Figure 9:
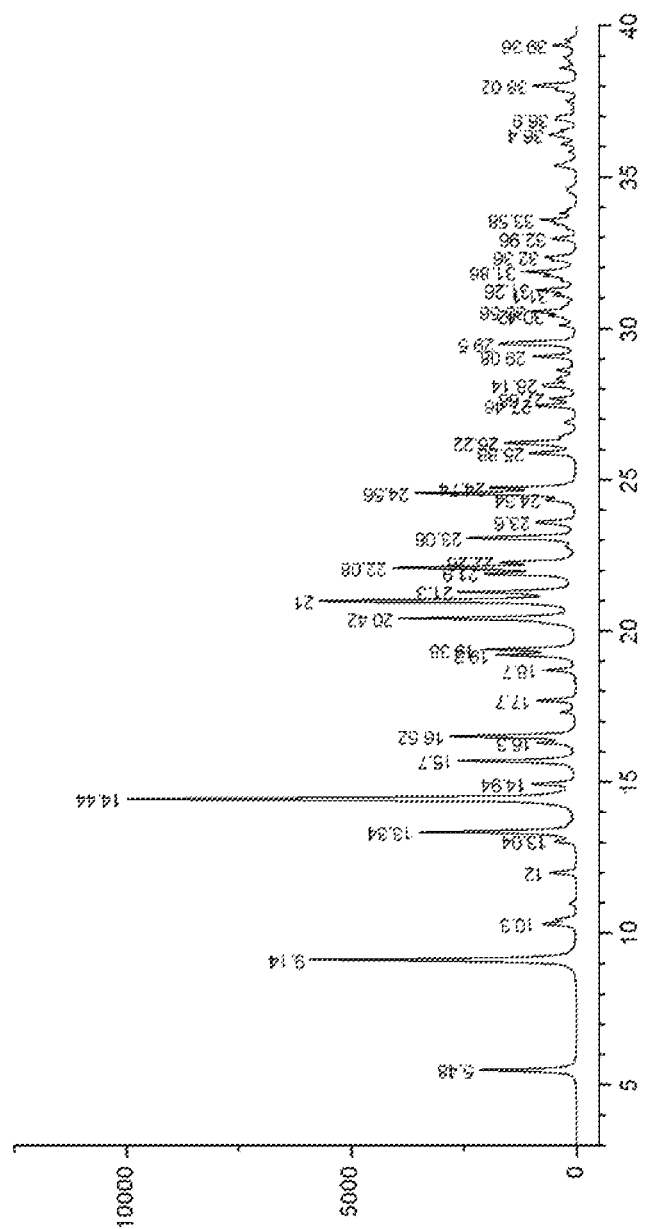
FIG. 9 is an X-ray powder diffraction pattern calculated from the single crystal in Example 4.

The following specific examples are intended to enable those skilled in the art to more clearly understand and implement the present application. They should not be considered as limiting the scope of the application, but are merely illustrations and typical representatives of the application. Those skilled in the art will understand that there are other synthetic routes for preparing the compounds of the present application, and the following are provided as non-limiting examples.

Example 1

Preparation of the Compound of Formula I

Step A: dimethyl L-homocysteinate dihydrochloride

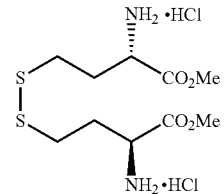

Under stirring in an ice bath, thionyl chloride (10.64 g, 89.4 mmol) was added dropwise into a suspension of L-homocysteine (8.0 g, 29.8 mmol) in methanol. The solution was gradually clear. After the addition was completed, the reaction solution was stirred for 10 min, followed by removing the ice bath, and stirred again at room temperature overnight. The solvent was removed, so as to give dimethyl L-homocysteinate dihydrochloride (10.6 g).

$^1$H-NMR (400 MHz, DMSO-d$_6$): δ=8.79 (s, 6H), 3.75 (s, 6H), 2.95-2.80 (m, 4H), 2.52-2.47 (m, 2H), 2.20-2.10 (m, 4H).

Step B: methyl (S)-2-amino-4-chlorosulfonylbutyrate hydrochloride

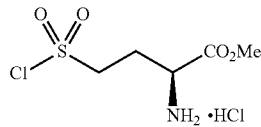

Under stirring in an ice bath, chlorine gas was introduced into a mixed solution of dimethyl L-homocysteinate dihydrochloride (10.6 g, 28.8 mmol) in ethanol (40 mL) and chloroform (80 mL) for 20 minutes, generating a white solid. The reaction solution was filtered and washed with chloroform, to give methyl (S)-2-amino-4-chlorosulfonylbutyrate hydrochloride (7.5 g).

$^1$H-NMR (400 MHz, DMSO-d$_6$): δ=13.46 (s, 1H), 8.57 (s, 2H), 3.66 (s, 3H), 3.18-2.95 (m, 2H), 2.52-2.45 (m, 1H), 2.22-1.97 (m, 2H).

Step C: methyl (S)-isothiazolidine-3-carboxylate 1,1-dioxide

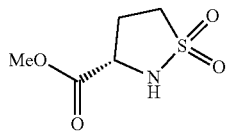 [SMILES: COC(=O)[C@@H]1CCS(=O)(=O)N1]

Under stirring in an ice-salt bath, a solution of triethylamine in chloroform was added dropwise into a suspension of methyl (S)-2-amino-4-chlorosulfonylbutyrate hydrochloride (4.5 g, 17.85 mmol) in chloroform. After the addition was completed, the ice-salt bath was removed. It was stirred at room temperature overnight and the solvent was removed. Then it was filtered through diatomite and washed with ethyl acetate. The solvent was removed to give a light yellow oil, namely methyl (S)-isothiazolidine-3-carboxylate 1,1-dioxide (3.2 g).

$^1$H-NMR (400 MHz, CDCl$_3$): δ=4.98 (s, 1H), 4.21 (dd, J=8.3, 4.6 Hz, 1H), 3.84 (s, 3H), 3.30-3.11 (m, 1H), 3.09-2.90 (m, 1H), 2.90-2.73 (m, 1H), 2.60 (ddd, J=18.4, 8.9, 4.7 Hz, 1H).

Step D: methyl (S)-2-(4-cyanopyridin-2-yl)isothiazolidine-3-carboxylate 1,1-dioxide

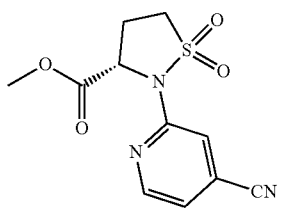 [SMILES: COC(=O)[C@@H]1CCS(=O)(=O)N1c1cc(C#N)ccn1]

Methyl (S)-isothiazolidine-3-carboxylate 1,1-dioxide (200 mg, 1.11 mmol), 2-bromo-4-cyanopyridine (204 mg, 1.11 mmol), cuprous iodide (105 mg, 0.55 mmol), N,N'-dimethylethylenediamine (98 mg, 1.11 mmol) and cesium carbonate (723 mg, 2.22 mmol) were added into a sealed tube reactor, dioxane (8 mL) was added thereto, nitrogen gas was introduced thereto for 5 min and the tube was sealed. They were reacted overnight at 80° C. After the starting materials were consumed, the solvent was removed and then separation by column chromatography (petroleum ether: ethyl acetate=1:1) was performed, to give the title compound methyl (S)-2-(4-cyanopyridin-2-yl)isothiazolidine-3-carboxylate 1,1-dioxide (230 mg).

$^1$H-NMR (400 MHz, CDCl$_3$): δ=8.40 (dd, J=5.2, 0.8 Hz, 1H), 7.69 (t, J=1.0 Hz, 1H), 7.19 (dd, J=5.2, 1.0 Hz, 1H), 5.01 (dd, J=8.0, 3.6 Hz, 1H), 3.78 (s, 3H), 3.64-3.55 (m, 1H), 3.48-3.42 (m, 1H), 2.95-2.84 (m, 1H), 2.65-2.52 (m, 1H).

Step E: (S)-2-(4-cyanopyridin-2-yl)isothiazolidine-3-carboxylic acid 1,1-dioxide

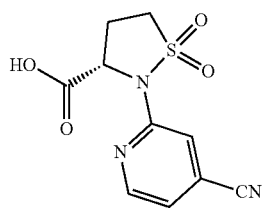 [SMILES: N#Cc1ccnc(N2[C@H](C(=O)O)CCS2(=O)=O)c1]

Under stirring in an ice bath, a suspension of lithium hydroxide was added dropwise into a solution of methyl (S)-2-(4-cyanopyridin-2-yl) isothiazolidine-3-carboxylate 1,1-dioxide (116 mg, 0.41 mmol) in methanol-tetrahydrofuran, reacting overnight. After the reaction was finished, it was diluted with 10 mL water, and extracted with ethyl acetate to remove impurities. The aqueous phase was added dropwise with 1N hydrochloric acid to make the pH thereof less than 5, and then extracted with ethyl acetate. The solvent was removed to give (S)-2-(4-cyanopyridin-2-yl) isothiazolidine-3-carboxylic acid 1,1-dioxide (103 mg).

$^1$H-NMR (400 MHz, DMSO-d$_6$): δ=13.5 (s, 1H), 8.54 (d, J=5.0, 1H), 7.51 (dd, J=3.74, 4.76 Hz, 1H), 7.45 (s, 1H), 4.95-4.90 (m, 1H), 3.75-3.60 (m, 2H), 2.85-2.72 (m, 1H), 2.46-2.38 (m, 1H).

Step F: (S)—N—((S)-1-(2-chlorophenyl)-2-((3,3-difluorocyclobutyl)amino)-2-oxoethyl)-2-(4-cyanopyridin-2-yl-N-(3-fluorophenyl)-isothiazolidine-3-carboxamide 1,1-dioxide

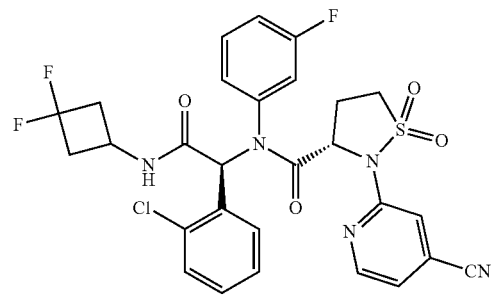 [SMILES: N#Cc1ccnc(N2[C@H](C(=O)N(c3cccc(F)c3)[C@H](C(=O)NC3CC(F)(F)C3)c3ccccc3Cl)CCS2(=O)=O)c1]

At room temperature, 3-amino-5-Fluorouridine (57 mg, 0.508 mmol) and o-chlorobenzaldehyde (72 mg, 0.512 mmol) were dissolved in methanol, and stirred for 30 min. (S)-2-(4-cyanopyridin-2-yl)isothiazolidine-3-carboxylic acid 1,1-dioxide (136 mg, 0.508 mmol) was then added into the mixed solution, stirred for 10 min, then added with 1,1-difluoro-3-isocyanocyclobutane (prepared according to the method described in patent CN103097340, 60 mg, 0.508 mmol), and stirred overnight. The solvent was removed and the residue was separated by thin layer chromatography, to give the title compound (S)—N—((S)-1-(2-chlorophenyl)-2-((3,3-difluorocyclobutyl)amino)-2-oxoethyl)-2-(4-cyanopyridin-2-yl-N-(3-fluorophenyl)-isothiazolidine-3-carboxamide 1,1-dioxide (the compound of formula I).

$^1$H-NMR (400 MHz, CDCl$_3$): δ=8.46 (m, 1H), 7.67 (d, J=8.8 Hz, 1H), 7.63 (s, 1H), 7.22-6.84 (m, 8H), 6.47 (d, J=3.6, 1H), 6.08 (s, 1H), 4.82 (d, J=6.1 Hz, 1H), 4.33 (m, 1H), 3.68-3.60 (m, 1H), 3.40-3.28 (m, 1H), 3.10-2.98 (m, 2H), 2.68-2.38 (m, 4H).

m/z=618 [M+H]$^+$.

Example 2

Preparation of Single Crystal of the Crystal of the Monohydrate of Formula II 1.0 g of the compound of formula I prepared in Example 1 was added to 2.5 mL of anhydrous methanol, stirred till the solution was clear, and filtered through the membrane. 2 mL of the above-mentioned filtrate was taken and added with 0.2 mL of water, and the solution was allowed to stand at room temperature and the crystal slowly precipitated, which is the single crystal of the crystal of the monohydrate of formula II.

Example 3

Cell Parameters of the Monohydrate Crystal of Formula II

The crystallographic data and atomic coordinates of the crystal of the monohydrate of formula II are shown in Tables 3, 4 and 5:

TABLE 3

Crystal data and structure refinement

| | |
|---|---|
| Empirical formula | $C_{28}H_{25}ClF_3N_5O_5S$ |
| formula weight | 636.04 |
| Temperature | 173(2)K |
| Wavelength | 1.54178 Å |
| crystal system | orthorhombic system |
| Space group | P21 21 21 |
| cell parameters | a = 8.7606(6) Å |
| | b = 10.1371(7) Å |
| | c = 32.183(2) Å |
| | α = 90 deg. |
| | β = 90 deg. |
| | γ = 90 deg. |
| Cell volume | 2858.0(3) Å$^3$ |
| Z | 4 |
| Calculated density | 1.478 Mg/m$^3$ |
| Absorption correction parameter | 2.466 mm$^{-1}$ |
| F(000) | 2679 |
| Crystal size | 0.05 × 0.04 × 0.03 mm |
| Angle range for data collection | 5.157 deg. to 66.672 deg. |
| hkl index range for collection | -10 <= h <= 10, -12 <= k <= 10, -38 <= l <= 38 |
| Reflection data collection/unique | 26530/5023 [R(int) = 0.0278] |
| data completeness to theta = 66.672 | 99.40% |
| Refinement method | F$^2$ full-matrix least-squares method |
| Data/restraints/parameters | 5023/2/400 |
| Goodness-of-fit on F$^2$ | 1.072 |
| Final R indices [I > 2 sigma(I)] | R1 = 0.0255, wR2 = 0.0680 |
| R indices (all data) | R1 = 0.0258, wR2 = 0.0682 |
| Absolute configuration parameters | 0.031(3) |
| Maximum difference between peak and hole | 0.334 and -0.264 e · Å$^{-3}$ |

TABLE 4

Atomic coordinates (×10$^4$) and equivalent isotropic displacement parameters (Å$^2$ × 10$^3$)

| | x | y | z | U (eq) |
|---|---|---|---|---|
| Cl(1) | 6119(1) | 5636(1) | 6560(1) | 46(1) |
| S(1) | 2239(1) | 3898(1) | 4898(1) | 25(1) |
| F(1) | 10806(2) | -1693(2) | 6727(1) | 69(1) |
| O(1) | 812(2) | 4211(2) | 4704(1) | 36(1) |
| N(1) | 3025(2) | 6374(2) | 5789(1) | 31(1) |
| C(1) | 2225(3) | 2294(2) | 5116(1) | 29(1) |
| F(2) | 9426(2) | -2883(2) | 6319(1) | 63(1) |
| O(2) | 3590(2) | 4158(2) | 4660(1) | 36(1) |
| N(2) | 2324(2) | 4673(2) | 5356(1) | 26(1) |
| C(2) | 1571(3) | 2503(2) | 5551(1) | 29(1) |
| F(3) | 364(2) | 1191(2) | 7207(1) | 58(1) |
| O(3) | 4966(2) | 3581(2) | 5647(1) | 31(1) |
| N(3) | 3999(2) | 3147(2) | 6284(1) | 24(1) |
| C(3) | 2261(2) | 3800(2) | 5716(1) | 24(1) |
| O(4) | 4775(2) | 431(2) | 6358(1) | 34(1) |
| N(4) | 7281(2) | 954(2) | 6298(1) | 31(1) |
| C(4) | 3873(2) | 3547(2) | 5879(1) | 23(1) |
| O(5) | 3977(2) | 1508(2) | 3803(1) | 45(1) |
| N(5) | 3480(3) | 9717(3) | 4504(1) | 48(1) |
| C(5) | 2731(2) | 5989(2) | 5399(1) | 26(1) |

TABLE 4-continued

Atomic coordinates (×10$^4$) and equivalent isotropic displacement parameters (Å$^2$ × 10$^3$)

| | x | y | z | U (eq) |
|---|---|---|---|---|
| C(6) | 2798(3) | 6845(2) | 5057(1) | 31(1) |
| C(7) | 3232(3) | 8133(2) | 5132(1) | 33(1) |
| C(8) | 3542(3) | 8561(2) | 5537(1) | 37(1) |
| C(9) | 3411(3) | 7639(2) | 5848(1) | 38(1) |
| C(10) | 3371(3) | 9024(2) | 4782(1) | 38(1) |
| C(11) | 5534(2) | 2735(2) | 6417(1) | 25(1) |
| C(12) | 5801(2) | 1253(2) | 6349(1) | 27(1) |
| C(13) | 7795(3) | -391(2) | 6264(1) | 33(1) |
| C(14) | 9500(3) | -583(3) | 6154(1) | 41(1) |
| C(15) | 9548(3) | -1642(3) | 6482(1) | 40(1) |
| C(16) | 8083(3) | -1153(3) | 6676(1) | 41(1) |
| C(17) | 2780(2) | 3266(2) | 6582(1) | 26(1) |
| C(18) | 2275(3) | 4508(2) | 6705(1) | 32(1) |
| C(19) | 1116(3) | 4613(3) | 6999(1) | 40(1) |
| C(20) | 470(3) | 3494(3) | 7171(1) | 40(1) |
| C(21) | 999(3) | 2287(3) | 7043(1) | 37(1) |
| C(22) | 2141(3) | 2132(2) | 6751(1) | 30(1) |
| C(23) | 5867(2) | 3143(2) | 6862(1) | 28(1) |
| C(24) | 5906(3) | 2245(2) | 7187(1) | 32(1) |
| C(25) | 6184(3) | 2648(3) | 7593(1) | 41(1) |
| C(26) | 6436(3) | 3966(3) | 7677(1) | 45(1) |
| C(27) | 6435(3) | 4877(3) | 7359(1) | 40(1) |
| C(28) | 6143(3) | 4460(2) | 6957(1) | 33(1) |

TABLE 5

Hydrogen atomic coordinates (×10$^4$) and isotropic displacement parameters (Å$^2$ × 10$^3$)

| | x | y | z | U(eq) |
|---|---|---|---|---|
| H(1) | 4300(400) | 1100(400) | 3610(80) | 1500(500) |
| H(1A) | 1571 | 1692 | 4952 | 35 |
| H(1B) | 3269 | 1925 | 5130 | 35 |
| H(2) | 3780(60) | 910(40) | 3965(14) | 120(20) |
| H(2A) | 1851 | 1757 | 5735 | 35 |
| H(2B) | 444 | 2566 | 5539 | 35 |
| H(3) | 1601 | 4186 | 5939 | 29 |
| H(4) | 7880(40) | 1540(30) | 6269(9) | 35(7) |
| H(6) | 2554 | 6551 | 4785 | 37 |
| H(8) | 3828 | 9447 | 5594 | 45 |
| H(9) | 3609 | 7918 | 6125 | 45 |
| H(11) | 6281 | 3212 | 6237 | 30 |
| H(13) | 7123 | -908 | 6073 | 40 |
| H(14A) | 9678 | -911 | 5868 | 49 |
| H(14B) | 10149 | 192 | 6215 | 49 |
| H(16A) | 8234 | -579 | 6922 | 49 |
| H(16B) | 7328 | -1856 | 6734 | 49 |
| H(18) | 2717 | 5279 | 6588 | 39 |
| H(19) | 767 | 5459 | 7083 | 48 |
| H(20) | -319 | 3560 | 7373 | 49 |
| H(22) | 2478 | 1280 | 6669 | 36 |
| H(24) | 5740 | 1337 | 7131 | 39 |
| H(25) | 6199 | 2019 | 7812 | 49 |
| H(26) | 6612 | 4246 | 7954 | 54 |
| H(27) | 6633 | 5781 | 7415 | 48 |

Example 4

Single-Crystal Calculation X-Ray Powder Diffraction Data for the Crystal of the Monohydrate of Formula II 1. Calculation software: Mercury 3.8 (Build RC2); wavelength: 1.54056.
2. X-ray powder diffraction data:

The peak positions and intensity of the characteristic peak of the X-ray powder diffraction spectrum calculated from the single crystal of the crystal of the monohydrate of formula II are shown in Table 6:

TABLE 6

| Nos. | 2θ (degree) | relative intensity (I/I$_0$) |
| --- | --- | --- |
| 1 | 5.48 | 16 |
| 2 | 9.14 | 62 |
| 3 | 10.30 | 9 |
| 4 | 12.00 | 6 |
| 5 | 13.34 | 26 |
| 6 | 14.44 | 100 |
| 7 | 14.94 | 10 |
| 8 | 15.70 | 24 |
| 9 | 16.52 | 34 |
| 10 | 17.70 | 9 |
| 11 | 18.70 | 7 |
| 12 | 19.20 | 21 |
| 13 | 19.38 | 15 |
| 14 | 20.42 | 42 |
| 15 | 21.00 | 61 |
| 16 | 21.30 | 31 |
| 17 | 21.90 | 23 |
| 18 | 22.08 | 52 |
| 19 | 22.26 | 22 |
| 20 | 23.08 | 31 |
| 21 | 23.60 | 6 |
| 22 | 24.56 | 35 |
| 23 | 24.74 | 23 |
| 24 | 25.88 | 8 |
| 25 | 26.22 | 19 |
| 26 | 27.46 | 10 |
| 27 | 27.68 | 7 |
| 28 | 28.14 | 8 |
| 29 | 29.08 | 12 |
| 30 | 29.50 | 21 |
| 31 | 30.56 | 12 |
| 32 | 31.26 | 9 |
| 33 | 31.86 | 10 |
| 34 | 32.36 | 8 |
| 35 | 32.96 | 5 |
| 36 | 33.58 | 7 |
| 37 | 36.40 | 7 |
| 38 | 38.02 | 12 |

Example 5

Preparation of the Crystal of the Monohydrate of Formula II 1.0 g of the compound of formula I prepared in Example 1 was added to 15 mL of methanol, stirred at room temperature till the solution was clear, and then added with 2 mL of water. The solution was cooled down to 0-5° C. with stirring, for crystallization. The crystal was filtered, and dried under reduced pressure at 40° C., to give 0.5 g of the crystal of the monohydrate of formula II.

Example 6

Preparation of the Crystal of the Monohydrate of Formula II 17 g of the compound of formula I prepared in Example 1 was added to 75 mL of anhydrous ethanol, heated to 60° C. with stirring till the solution was clear, and then added with 1.5 mL of water. The solution was cooled down to 0-5° C. with stirring, for crystallization. The crystal was filtered, and dried under reduced pressure at 40° C., to give 15.8 g of the crystal of the monohydrate of formula II.

Example 7

Preparation of the Crystal of the Compound of Formula I 1.0 g of the compound of formula I prepared in Example 1 was added to 5 mL of anhydrous dichloromethane, and stirred at room temperature till the solution was clear. The solution was then added with 1 g of 4A molecular sieve, and dried with stirring for 2 hours. The mixture was filtered under nitrogen protection. The filtrate was concentrated under reduced pressure at room temperature to remove a half volume of the solvent, transferred to −10° C., and stirred under nitrogen protection to crystallization, followed by filtration. The filter cake was dried under reduced pressure at 40° C., to give the crystal of the compound of formula I.

Example 8

Preparation of the Crystal of the Compound of Formula I 1.5 g of the compound of formula I prepared in Example 1 was added to 10 mL of anhydrous isopropanol, and heated to 60° C. with stirring till the solution was clear. The solution was then added with 2 g of 4A molecular sieve, and dried with stirring for 2 hours. The mixture was filtered under nitrogen protection. The filtrate was sealed, then naturally cooled down to room temperature and stirred to crystallization under nitrogen protection, followed by filtration. The filter cake was dried under reduced pressure at 40° C., to give the crystal of the compound of formula I.

Example 9

Amorphous Form of the Compound of Formula I 1.5 g of the compound of formula I prepared in Example 1 was added to 10 mL of anhydrous dichloromethane, and stirred at room temperature till the solution was clear. The solution was concentrated under reduced pressure to give a solid. The solid was then dried under reduced pressure at 40° C., to give an amorphous form of the compound of formula I.

Example 10

Amorphous Form of the Compound of Formula I 1 g of the compound of formula I prepared in Example 1 was added to a mixed solvent of anhydrous ethyl acetate (1 mL) and anhydrous dichloromethane (8 mL), and stirred at room temperature till the solution was clear. The solution was then concentrated under reduced pressure to give a solid. Subsequently, the solid was dried under reduced pressure at 40° C., to give an amorphous form of the compound of formula I.

Test Example 1

Stability Testing for the Crystal of the Monohydrate of Formula II

In accordance with "Stability Testing of New Drug Substances and Products" in ICH Q1A and "Guidelines for the Stability Testing of Drug Substances and Preparations" in Pharmacopoeia of China, fourth part, 2015 edition, 9001, the stability influencing factors were tested for the crystal of the monohydrate formula II, including high temperature, high humidity and light tests. The results are shown in Tables 7, 8 and 9:

TABLE 7

Stability results of high temperature test

| Item | 0 (day) | High temperature test (40° C.) | | High temperature test (60° C.) | |
|---|---|---|---|---|---|
| | | 5 (day) | 10 (day) | 5 (day) | 10 (day) |
| Appearance | White powder | White powder | White powder | White powder | White powder |
| Total impurities (%) | 0.38 | 0.45 | 0.47 | 0.48 | 0.47 |
| Enantiomers (%) | 0.01 | 0.01 | 0.01 | ND | 0.01 |
| Total of diastereoisomers (%) | 0.05 | 0.05 | 0.05 | 0.05 | 0.05 |
| Water (%) | 3.10 | 2.69 | 2.45 | 2.67 | 2.51 |

Note:
ND means not detected.

TABLE 8

Stability results of high humidity test

| Item | 0 (day) | High humidity test (75% RH) | | High humidity test (92.5% RH) | |
|---|---|---|---|---|---|
| | | 5 (day) | 10 (day) | 5 (day) | 10 (day) |
| Appearance | White powder | White powder | White powder | White powder | White powder |
| Total impurities (%) | 0.38 | 0.44 | 0.50 | 0.49 | 0.49 |
| Enantiomers (%) | 0.01 | 0.01 | 0.01 | 0.01 | 0.01 |
| Total of diastereoisomers (%) | 0.05 | 0.05 | 0.05 | 0.04 | 0.05 |
| Water (%) | 3.10 | 2.69 | 2.53 | 2.72 | 2.42 |

TABLE 9

Stability results of light test

| Item | 0 (day) | Lighting | | shading | |
|---|---|---|---|---|---|
| | | 5 (day) | 10 (day) | 5 (day) | 10 (day) |
| Appearance | White powder | White powder | White powder | White powder | White powder |
| Total impurities (%) | 0.38 | 0.56 | 0.63 | 0.49 | 0.47 |
| Enantiomers (%) | 0.01 | 0.01 | 0.01 | 0.01 | 0.01 |
| Total of diastereoisomers (%) | 0.05 | 0.05 | 0.05 | 0.05 | 0.05 |
| Water (%) | 3.10 | 2.72 | 2.47 | 2.73 | 2.55 |

Test Example 2

Stability Testing of the Crystal of the Compound of Formula I

In accordance with "Stability Testing of New Drug Substances and Products" in ICH Q1A and "Guidelines for the Stability Testing of Drug Substances and Preparations" in Pharmacopoeia of China, fourth part, 2015 edition, 9001, the stability influencing factors were tested for the crystal of the compound of formula I, including high temperature and high humidity tests. The results are shown in Tables 10 and 11:

TABLE 10

Stability results of high temperature test

| Item | 0 (day) | High temperature test (40 °C.) | | High temperature test (60° C.) | |
|---|---|---|---|---|---|
| | | 5 (day) | 12 (day) | 5 (day) | 12 (day) |
| Appearance | White powder | White powder | White powder | White powder | White powder |
| Total impurities (%) | 0.39 | 0.42 | 0.37 | 0.63 | 0.54 |
| Water (%) | 0.45 | 0.85 | 0.85 | 0.59 | 0.73 |

TABLE 11

Stability results of high humidity test

| Item | 0 (day) | High humidity test (75% RH) | | High humidity test (92.5% RH) | |
|---|---|---|---|---|---|
| | | 5 (day) | 12 (day) | 5 (day) | 12 (day) |
| Appearance | White powder | White powder | White powder | White powder | White powder |
| Total impurities (%) | 0.39 | 0.43 | 0.37 | 0.47 | 0.37 |
| Water (%) | 0.45 | 0.94 | 1.16 | 1.58 | 1.75 |

Test Example 3

Stability Testing of Amorphous Form of the Compound of Formula I

In accordance with "Stability Testing of New Drug Substances and Products" in ICH Q1A and "Guidelines for the Stability Testing of Drug Substances and Preparations" in Pharmacopoeia of China, fourth part, 2015 edition, 9001, the stability influencing factors were tested for the amorphous form of the compound of formula I, including high temperature and high humidity tests. The results are shown in Tables 12 and 13:

TABLE 12

Stability results of high temperature test

| Item | 0 (day) | High temperature test (40° C.) | | | High temperature test (60° C.) | | |
|---|---|---|---|---|---|---|---|
| | | 5 (day) | 10 (day) | 30 (day) | 5 (day) | 10 (day) | 30 (day) |
| Appearance | White powder | White powder | White powder | White powder | White powder | White powder | White powder |

TABLE 12-continued

Stability results of high temperature test

| Item | High temperature test (40° C.) | | | High temperature test (60° C.) | | |
|---|---|---|---|---|---|---|
| | 0 (day) | 5 (day) | 10 (day) | 30 (day) | 5 (day) | 10 (day) | 30 (day) |
| Total impurities (%) | 0.28 | 0.25 | 0.28 | 0.26 | 0.31 | 0.27 | 0.28 |
| Water (%) | 1.4 | 1.1 | 1.0 | 0.8 | 0.8 | 0.6 | 0.5 |

TABLE 13

Stability results of high humidity test

| Item | High humidity test (75% RH) | | | High humidity test (92.5% RH) | | |
|---|---|---|---|---|---|---|
| | 0 (day) | 5 (day) | 10 (day) | 30 (day) | 5 (day) | 10 (day) | 30 (day) |
| Appearance | White powder | White powder | White powder | White powder | White powder | White powder | White powder |
| Total impurities (%) | 0.28 | 0.30 | 0.30 | 0.27 | 0.30 | 0.29 | 0.26 |
| Water (%) | 1.4 | 1.7 | 1.8 | 1.8 | 2.1 | 2.3 | 2.4 |

Test Example 4

Bioactivity Experiments

Enzyme Assay:

Resazurin is a traditional redox dye, and after a redox reaction, it can be reduced from a blue resazurin without fluorescence to a pink fluorescent substance, resorufin, which can be measured and quantified with relative fluorescence unit (RFU) of fluorophotometer (Ex=530-570 nm, Em=590-620 nm). At present, resazurin is widely used for determining the viability of bacteria, cells, etc., and the enzyme activity detection of oxidoreductase. We detected the decrease of cofactor NADPH to determine the inhibitory activity of a compound against IDH1m and detected the generation of cofactor NADPH to determine the inhibitory activity of a compound against IDH WT. The compound was pre-incubated with IDH1m and NADPH, and then the reaction was initiated by adding α-KG and performed for certain time under a linear condition. Then, diaphorase (lipoamide dehydrogenase) and the corresponding substrate resazurin were added thereto for detection. Lipoamide dehydrogenase terminated the IDH1m reaction by decreasing the available cofactor NADPH, which oxidized NADPH to NADP, and reduced resazurin to high fluorescent resorufin. The amount of the remaining cofactor NADPH after a specific reaction time was quantified via an easily detectable fluorophore.

The compound was pre-incubated with IDH-WT and NADP, and then the reaction was initiated by adding isocitric acid, diaphorase (lipoamide dehydrogenase) and the corresponding substrate resazurin, and performed for certain time under a linear condition, followed by detecting the amount of fluorescent substance. NADP was reduced to NADPH in this experiment, and the latter reduced resazurin to high fluorescent resorufin under the action of lipoamide dehydrogenase. The amount of the generated cofactor NADPH after a specific reaction time was quantified via a detectable fluorophore, so as to calculate the inhibitory effect of the compound on IDH-WT.

The specific operation was as follows: 2.5 μl of the compound diluted in a 3-fold gradient was added to a 384-well plate, followed by adding 5 μl of the reaction buffer (20 mM Tris-HCl, pH 7.5; 150 mM NaCl; 10 mM $MgCl_2$; 0.4 mg/mL BSA (Bovine Serum Albumin) and 2 mM DTT (dithiothreitol)) containing 40 nM IDH1 (R132H/R132C) and 20 μM NADPH. Then, the above test mixture was incubated at 23° C. for 16 hours, and then 2.5 μl of the reaction buffer containing 4 mM α-KG was added to initiate the reaction. After they were incubated for 60 minutes at room temperature, 5 μl of the termination mixture (0.4 U/ml diaphorase and 20 μM resazurin) formulated with the reaction buffer was added to convert resazurin to resorufin, so as to measure the amount of the remaining NADPH. After incubating at 23° C. for 10 minutes, fluorescence values were determined through Flexstation 3 at Ex535/Em595. The enzyme activity of the compound was respectively determined at 12 concentrations, and the data were calculated using the software GraFit6.0 (Erithacus Software) to obtain the $IC_{50}$ value of the compound.

2-HG determination:

In the presence of 2-HG, phosphoglycerate dehydrogenase PHGDH can reduce NAD to NADPH, and the latter may be quantitatively determined by lipoamide dehydrogenase and the substrate thereof, resazurin.

HT-1080 cell is a human fibrosarcoma cell line with an IDH1 mutation (R132C). U87 cell is a human glioblastoma cell line with an IDH1 mutation (R132H). They were cultured in RPMI-1640 medium supplemented with 10% fetal bovine serum, 100 units/mL penicillin and 0.1 mg/mL streptomycin.

Cells was digested with trypsin, and inoculated into a 6-well plate at a density of $5 \times 10^5$, and cultured overnight in an incubator at 37° C. Next day, the test compound was added (the final concentration of DMSO is 0.1%) thereto and cultured for another 24 hours. Culture medium of each sample was sucked out and centrifuged at 1000 rpm for 10 min. The supernatant was sucked out to detect the content of 2-HG therein. Additionally, cells were washed with PBS (phosphate buffered saline), digested with trypsin and collected. After the collected cells were washed with PBS for one time, the determination of intracellular 2-HG content was performed.

The method for determining the intracellular 2-HG was as follows: cells were re-suspended with 300 μL reaction buffer (40 mM Tris-HCl, pH 8.5; 150 mM NaCl) and disrupted by ultrasonication. They were centrifuged for 10 min at 12,000 rpm and 4° C. to remove insoluble substances. 25 μL supernatant was sucked out to determine the protein concentration by a BCA kit. Another 200 μL supernatant was transferred to a new group of centrifuge tubes, each of which was added with 4 μL of 3 M HCl, placed at room temperature for 5 min and centrifuged at 12,000 rpm for 5 min at room temperature. 100 μL supernatant was sucked out and transferred to a 96-well "V" bottom plate, and 3.6 μL of 2 M Tris base (tromethamine) was added to each well, it was placed at room temperature for 5 min and centrifuged at 12,000 rpm for 2 min. The pH was approximately equal to 8.0 through detection by pH test paper.

Preparation of standard curve of 2-HG: 2-HG stock solution was diluted to 500 μM with reaction buffer, and then 200 μL was taken therefrom for a 2-fold gradient dilution, 10 concentrations in total. The following operations were same as described above, including the steps for acid treatment and alkali neutralization.

The aforementioned samples, the test cell samples or standard samples, were diluted in 5 folds, and then 5 μL of each sample was taken therefrom and added to a 384-well plate. 10 μL of the detection mixture (8 μM PHGDH (phosphoglycerate dehydrogenase); 0.5 mM NAD; 0.1 U/mL diaphorase and 10 μM resazurin) was added to each well, and they were reacted for 60 min at 23° C. Fluorescence values were determined through Flexstation 3 at Ex535/Em595.

The measured fluorescence values were compared after being corrected with the protein concentrations of the corresponding samples.

The method for determining extracellular 2-HG was as follows: 500 μL of each culture medium supernatant was taken. 10 μL of 3 M HCl was added into each tube and placed for 5 min at room temperature. Then, 18 μL of 2 M Tris base was added into each tube and placed for 5 min at room temperature. It was centrifuged at 12,000 rpm for 2 min. The pH was approximately equal to 8.0 detected by pH test paper. Preparation of standard curve of 2-HG: 2-HG stock solution was diluted to 500 μM with complete medium, and then 500 μL was taken therefrom for a 2-fold gradient dilution, 10 concentrations in total. The following operations were same as described above, including the steps for acid treatment and alkali neutralization. The aforementioned samples, the test culture supernatant samples or standard samples, were diluted in 5 folds, and then 5 μL was taken therefrom and added to a 384-well plate. 10 μL of the detection mixture (8 μM PHGDH; 0.5 mM NAD; 0.1 U/mL diaphorase and 10 μM resazurin) was added to each well and reacted for 60 min at 23° C. Fluorescence values were determined through Flexstation 3 at Ex535/Em595.

The compound of formula I was analyzed according to the biological methods herein, and the results are as follows:

The inhibitory activities ($IC_{50}$) of the compound of formula I against IDH1 mutants (R132H and R132C) are shown in Table 14.

TABLE 14

| Compound | IDH1(R132H) $IC_{50}$ (nM) | IDH1(R132C) $IC_{50}$ (nM) |
|---|---|---|
| Compound of formula I | <20 | <20 |

Test Example 3

Pharmacokinetic Experiments

Male SD rats were from Beijing Vital River Laboratory Animal Technology Co., Ltd., and divided into groups (3 rats per group). The rats were intragastrically administered with the test sample suspension (5 mg/kg) via a single peroral administration, respectively. The animals were fasted overnight before this study. The fasting time period was from 10 hours before administration to 4 hours after administration. Blood samples were taken at 0.25, 0.5, 1, 2, 4, 6, 8 and 24 hours after administration. After the rats were anesthetized with isoflurane using an anesthesia machine for small animal, and then 0.3 mL whole blood samples were taken from the fundus venous plexus. The blood samples were placed in heparin anticoagulant tubes, and centrifuged for 5 min at 4° C. and 4000 rpm. The plasma was transferred to centrifuge tubes, and stored at −80° C. till analysis. The samples in plasma were extracted through protein precipitation. The liquid extract was analyzed by LC-MS/MS, wherein HPLC conditions were as follows: flow rate 0.4 mL/min; mobile phase A: water/formic acid (99.9/0.1, v/v); mobile phase B: acetonitrile/formic acid (99.9/0.1, v/v); injection volume: 5 μL; column temperature: RT; autosampler temperature: RT; run time: 2.5 min.

Pharmacokinetic data of the compound of formula I is shown in Table 15:

TABLE 15

| | The compound of Formula I |
|---|---|
| Gender of rata | male |
| Oral dose (mg/kg) | 5 |
| $T_{1/2}$(hr) | 10.7 |
| Tmax(hr) | 4.0 |
| Cmax(ng/mL) | 556 |
| $AUC_{INF\_obs}$(hr*ng/mL) | 10567 |
| Formulation of dosage forms | 0.5% MC, 0.2% Tween80 |

What is claimed is:

1. A crystalline form of a monohydrate of (S)—N—((S)-1-(2-chlorophenyl)-2-((3,3-difluorocyclobutyl)amino)-2-oxoethyl)-2-(4-cyanopyridin-2-yl)-N-(3-fluorophenyl)-isothiazolidine-3-carboxamide 1,1-dioxide represented by formula II,

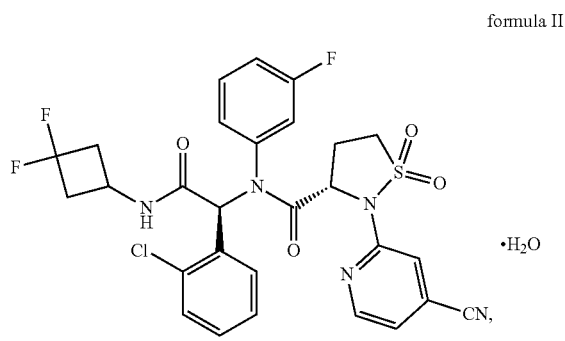 [SMILES: N#Cc1ccnc(N2[C@H](C(=O)N(c3cccc(F)c3)[C@H](C(=O)NC3CC(F)(F)C3)c3ccccc3Cl)CCS2(=O)=O)c1 ; O]

formula II

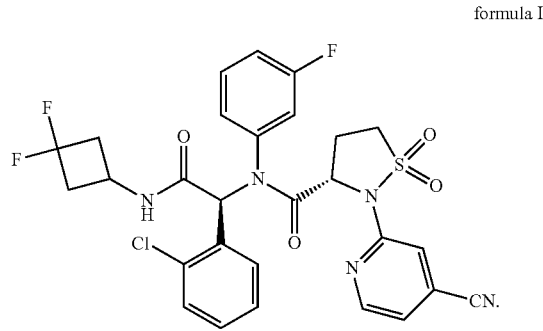 [SMILES: N#Cc1ccnc(N2[C@H](C(=O)N(c3cccc(F)c3)[C@H](C(=O)NC3CC(F)(F)C3)c3ccccc3Cl)CCS2(=O)=O)c1]

formula I wherein the X-ray powder diffraction spectrum thereof has diffraction peaks at 14.40°±0.2°, 20.28°±0.2°, 20.94°±0.2°, 22.02°±0.2° and 24.46°±0.2°, represented by 2θ values.

2. The crystalline form of the monohydrate of formula II according to claim 1, wherein the X-ray powder diffraction spectrum thereof has diffraction peaks at 9.12°±0.2°, 13.32°±0.2°, 14.40°±0.2°, 15.64°±0.2°, 16.46°±0.2°, 20.28°±0.2°, 20.94°±0.2°, 22.02°±0.2°, 22.98°±0.2°, 24.46°±0.2° and 29.34°±0.2°, represented by 2θ values.

3. The crystalline form of the monohydrate of formula II according to claim 2, wherein the X-ray powder diffraction spectrum thereof has diffraction peaks at 5.52°±0.2°, 9.12°±0.2°, 10.30°±0.2°, 10.48°±0.2°, 11.96°±0.2°, 13.32°±0.2°, 14.40°±0.2°, 14.90°±0.2°, 15.64°±0.2°, 16.46°±0.2°, 17.28°±0.2°, 17.58°±0.2°, 18.60°±0.2°, 19.14°±0.2°, 19.32°±0.2°, 20.28°±0.2°, 20.94°±0.2°, 21.20°±0.2°, 22.02°±0.2°, 22.98°±0.2°, 23.52°±0.2°, 24.46°±0.2°, 25.74°±0.2°, 26.06°±0.2°, 26.74°±0.2°, 27.32°±0.2°, 27.98°±0.2°, 28.40°±0.2°, 28.90°±0.2°, 29.34°±0.2°, 30.36°±0.2°, 31.00°±0.2°, 31.74°±0.2°, 32.22°±0.2°, 32.82°±0.2°, 33.32°±0.2° and 37.84°±0.2°, represented by 2θ values.

4. The crystalline form of the monohydrate of formula II according to claim 1, wherein the differential scanning calorimetry (DSC) measurement pattern thereof has an onset point at 186° C.±5° C.

5. A crystal composition, characterized in that the crystalline form of the monohydrate of formula II according to claim 1 represents 50% or more of the weight of the crystal composition.

6. A pharmaceutical composition, comprising the crystalline form of the monohydrate of formula II according to claim 1.

7. A method for treating IDH1 mutation-induced cancer, comprising administering a therapeutically effective amount of the crystalline form of the monohydrate of formula II according to claim 1 to a subject in need thereof.

8. A method of preparing the crystalline form of the monohydrate of formula II according to claim 1, comprising: (1) dissolving a compound of formula I in an organic solvent, and stirring till the solution is clear, wherein the organic solvent is selected from one or more of methanol, ethanol, isopropanol, ethylene glycol, propylene glycol, acetone, tetrahydrofuran, acetonitrile, dichloromethane, or ethyl acetate; (2) adding water to the solution obtained in step (1); and (3) cooling down the solution to crystallization, filtering and drying, 9. The method according to claim 8, wherein in step (1), the organic solvent is selected from one or more mixed solvents of methanol, ethanol, isopropanol, ethylene glycol, propylene glycol, acetone, tetrahydrofuran, acetonitrile, dichloromethane, or ethyl acetate.

10. The method according to claim 8, wherein in step (1), the molar volume ratio of the compound of formula I to the organic solvent is 1 mmol: 2-20 mL.

11. The method according to claim 8, wherein in step (1), the temperature for dissolving the compound of formula I in the organic solvent is 20° C. to 100° C.

12. The method according to claim 8, wherein the molar volume ratio of the compound of formula I in step (1) to the water in step (2) is 1 mmol: 0.01-5 mL.

13. A crystalline form of (S)—N—((S)-1-(2-chlorophenyl)-2-((3,3-difluorocyclobutyl)amino)-2-oxoethyl)-2-(4-cyanopyridin-2-yl)-N-(3-fluorophenyl)-isothiazolidine-3-carboxamide 1,1-dioxide represented by formula I, formula I wherein the X-ray powder diffraction spectrum thereof has diffraction peaks at 8.64°±0.2°, 9.34°±0.2°, 20.72°±0.2°, 21.30°±0.2° and 24.02°±0.2°, represented by 2θ values.

14. The crystalline form of the compound of formula I according to claim 13, wherein the X-ray powder diffraction spectrum thereof has diffraction peaks at 8.64°±0.2°, 9.34°±0.2°, 14.62°±0.2°, 19.66°±0.2°, 20.04°±0.2°, 20.46°±0.2°, 20.72°±0.2°, 21.30°±0.2°, 22.46°±0.2°, 24.02°±0.2° and 27.42°±0.2°, represented by 2θ values.

15. The crystalline form of the compound of formula I according to claim 14, wherein the X-ray powder diffraction spectrum thereof has diffraction peaks at 8.64°±0.2°, 9.34°±0.2°, 11.18°±0.2°, 12.80°±0.2°, 13.68°±0.2°, 14.62°±0.2°, 15.18°±0.2°, 15.58°±0.2°, 16.36°±0.2°, 17.04°±0.2°, 17.60°±0.2°, 18.14°±0.2°, 18.40°±0.2°, 18.88°±0.2°, 19.66°±0.2°, 20.04°±0.2°, 20.46°±0.2°, 20.72°±0.2°, 21.30°±0.2°, 22.16°±0.2°, 22.46°±0.2°, 22.92°±0.2°, 23.16°±0.2°, 24.02°±0.2°, 24.32°±0.2°, 24.92°±0.2°, 25.14°±0.2°, 25.48°±0.2°, 25.92°±0.2°, 26.30°±0.2°, 27.42°±0.2°, 27.84°±0.2°, 28.46°±0.2° 30.16°±0.2°, 30.98°±0.2° and 33.18°±0.2°, represented by 2θ values.

16. The crystalline form of the compound of formula I according to claim 13, wherein the differential scanning calorimetry (DSC) measurement pattern thereof has an onset point at 103° C.±5° C.

17. A method for preparing the crystalline form of the (S)—N—((S)-1-(2-chlorophenyl)-2-((3,3-difluorocyclobutyl)amino)-2-oxoethyl)-2-(4-cyanopyridin-2-yl)-N-(3-fluorophenyl)-isothiazolidine-3-carboxamide 1,1-dioxide of formula I according to claim 13, comprising: (1) dissolving the (S)—N—((S)-1-(2-chlorophenyl)-2-((3,3-difluorocyclobutyl)amino)-2-oxoethyl)-2-(4-cyanopyridin-2-yl)-N-(3-fluorophenyl)-isothiazolidine-3-carboxamide 1,1-dioxide of formula I in an anhydrous organic solvent, stirring till the solution is clear, and added with 4A molecular sieve to drying, wherein the anhydrous organic solvent is selected from one or more of dichloromethane, isopropanol, n-hexane, ethyl acetate, or methyl tert-butyl ether; (2) filtering under nitrogen protection, and cooling down the filtrate to crystallization; and (3) filtering under nitrogen protection and drying

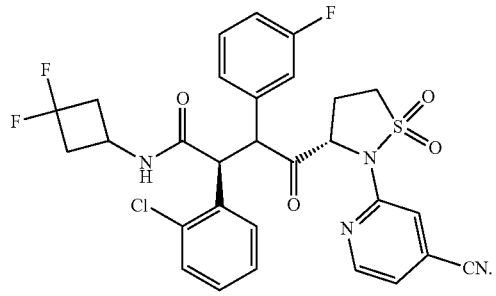

formula I

18. A crystal composition, wherein the crystalline form of the compound of formula I according to claim 13 represents 50% or more of the weight of the crystal composition.

19. A pharmaceutical composition comprising the crystalline form of the compound of formula I according to claim 13.

20. A method for treating IDH1 mutation-induced cancer, comprising administering a therapeutically effective amount of the crystalline form of the compound of formula I according to claim 13 to a subject in need thereof.

* * * * *